United States Patent [19]

Hajime

[11] Patent Number: 4,868,404
[45] Date of Patent: Sep. 19, 1989

[54] SURFACE INSPECTION APPARATUS USING A MASK SYSTEM TO MONITOR UNEVEN SURFACES

[75] Inventor: Yoshida Hajime, Tokyo, Japan

[73] Assignee: Hajime Industries, Ltd., Tokyo, Japan

[21] Appl. No.: 179,052

[22] Filed: Apr. 8, 1988

[30] Foreign Application Priority Data

Apr. 23, 1987 [JP] Japan .................................. 62-100765
Jun. 9, 1987 [JP] Japan .................................. 62-143779

[51] Int. Cl.⁴ ........................................... G01N 21/88
[52] U.S. Cl. ................................ 250/572; 250/223 B; 356/240
[58] Field of Search ................... 250/571, 572, 237 R, 250/237 G, 223 B; 209/524, 526; 356/237, 240, 445

[56] References Cited

U.S. PATENT DOCUMENTS

| | | | |
|---|---|---|---|
| 3,953,739 | 4/1976 | Colombo et al. | 250/571 |
| 4,139,307 | 2/1979 | Clarke | 250/571 |
| 4,376,583 | 3/1983 | Alford et al. | 250/572 |
| 4,402,607 | 9/1983 | McVay et al. | 250/224 |
| 4,629,319 | 12/1986 | Clarke et al. | 356/237 |
| 4,632,546 | 12/1986 | Sick et al. | 356/237 |
| 4,687,338 | 8/1987 | Task et al. | 356/237 |
| 4,710,642 | 12/1987 | McNeil | 250/571 |
| 4,715,709 | 12/1987 | Sekine et al. | 356/237 |
| 4,741,621 | 5/1988 | Taft et al. | 356/237 |
| 4,759,073 | 7/1988 | Yamane et al. | 356/237 |
| 4,780,600 | 10/1988 | Johnston | 250/237 G |

*Primary Examiner*—David C. Nelms
*Assistant Examiner*—Stephone B. Allen
*Attorney, Agent, or Firm*—Bauer & Schaffer

[57] ABSTRACT

A surface inspection apparatuses having a light source for irradiating an uneven surface of an object to be inspected, a photoelectric conversion sensor for picking up the uneven surface of the object and generating a video signal thereof, and an electronic processor for processing the video signal to inspect the surface of the object, in which an optical mask is located in front of the light source so as to restrict the passage of the light from the light source with a predetermined pattern, whereby the irregular light reflection of the light from the light source, which passed through the optical mask, on the uneven surface becomes substantially uniform.

9 Claims, 6 Drawing Sheets

SURFACE INSPECTION APPARATUS USING A MASK SYSTEM TO MONITOR UNEVEN SURFACES

BACKGROUND OF THE INVENTION

1. Field of the Invention

The present invention relates generally to surface inspection apparatuses, and is directed specifically to a surface inspection apparatus that inspects whether or not there are such defects as flaws, dirty, hit marks, etc., on the surface of an object which is, for example, a bottle cap or beer can end (bottom and top, or the like).

2. Description of the Prior Art

A cap for a bottle or an end for a beer can or the like is generally made of plastic material or metal whereas its flat surface (its top or bottom surface) is round-shaped. Further, on such cap or end it is normal that a plurality of concentric circular-shaped (ring-shaped) or spiral-shaped unevenness or grooves are formed in order that the cap or the like sufficiently withstands the pressure variations as caused by the liquids within such containers, or in other words in order to increase the strength of the cap or the like.

FIG. 1A is a top plan view of a cap 1 for a bottle that is made of metal as one example of an object to be inspected, and FIG. 1B is a cross section diagram taken along the line B-B in FIG. 1A. In the figures, a, b and c are concentric circular-shaped unevennesses, whereas a is a ring-shaped protrusion that protrudes upwards from the surface of cap 1 while b and c are respectively ring-shaped edge lines of steps that are formed on the surface of cap 1 at the inside portion of the ring-shaped protrusion a.

FIG. 2 is a schematic diagram which shows an example of a surface inspection apparatus of the conventional art that inspects the existence or not of flaws such as surface scratches or the like on the surface of cap 1 for the bottle as the inspected object as shown on FIG. 1. In FIG. 2, there is provided a light source 2 such as a lamp that irradiates the surface of cap 1. In this case, since the cap 1 has on its surface unevenness, in order to irradiate the vertical surfaces or walls thereof also, the light source 2 is placed off to an upper angled location of the cap 1. There is provided a photoelectric conversion sensor 3 such as a video camera which generates a video signal upon receiving the reflection light from the surface of cap 1 as the light is irradiated thereon from the light source 2. This video camera 3 is located above the cap 1 in a manner that the optical light axis thereof coincides to the center axis X of cap 1 which is perpendicular to the surface of cap 1 and at the same time passes the center point 0 of the cap 1. An electronic processor 4 is provided which is formed of a computer, etc., and analyzes and processes the video signal from the video camera 3 and then judges the good or bad of the surface of cap 1.

Further, FIG. 3 is a plan view that shows the relation of cap 1 and the light source 2 as shown on FIG. 2.

Now then, the light from the light source 2, that is placed off to the upper-angled location of the cap 1, is irregularly reflected on the surface of cap 1, and a part of such irregularly reflected light is picked up by the photoelectric conversion sensor or the video camera 3 which then generates the video signal of the image of the surface of cap 1. This video signal is then processed by the electronic processor 4 so that such flaws as scratches or dirties that appear as abnormally dark or extremely bright spots on the surface of cap 1 are detected so as to make the judgement of whether the surface of the cap 1 is good or bad.

In this case, as shown in FIG. 3, for the light of the center portion among the lights emitted from the light source 2, that is, the light which goes on substantially along an optical axis A of the light source 2, portions a', b' and c' of the ring-shaped protrusions a as well as the ring-shaped boundaries b and c on the surface of the cap 1, which portions a', b' and c' are positioned at the side to the light source 2 with respect to the center 0 of the cap 1 and shown by thick lines, and a portion a" of the ring-shaped protrusion a which is located at the side opposite to the portion a' with respect to the center O, are portions that stand up like walls as will be clear from Figs. 1B and 2. The light from the light source 2 is irregularlly reflected on these portions a', b',c' and a" drastically excessive as compared with the other portions and as a matter of fact, such irregularly reflected lights on such portions a', b', c' and a" are directly picked up by the video camera 3. On the other hand, the majority of the lights that are irregularly reflected on the portions of the same ring-shaped protrusion a as well as boundaries b, c, which stand up like a wall except the portions a', b', c' and a", propagate in the directions as shown by arrow marks d as in FIG. 3, and do not directly reach the video camera 3. It is without question that a part of the light, which is irregularly reflected under normal conditions on the flat surface portion of cap 1, is picked up by the video camera 3 which then produces the video signal of cap 1. The video signal from the video camera 3 is supplied to the electronic processor 4 which processes the video signal same as aforementioned to judge the existence or not of flaws on cap 1 or rather whether the cap 1 is good or bad. Further, the angular range ARC of the arc portions a', a", b' and c' is smaller than 90° as centered against the optical axis A.

As mentioned above at the conventional apparatuses, the lights, that are irregularly reflected on the portions a', b', c' and a" on the surface of cap 1, contain drastically excessive irregularly reflection lights in comparision to those of the other portions and since such irregularly reflected lights directly reach the video camera 3, such above mentioned portions a', b', c' and a" appear to be distinctly brighter than the other portions in the video camera 3. Thus, it not only causes the inspection of the existence or not of flaws at these portions a', b', c' and a" to be impossible, but also causes bad influences on the inspection of the other portions. As attempts to resolve such problems, inspection is conducted only on other portions by excluding these portions that cause extreme irregular reflections on the surface of cap 1 or otherwise, while attempting to select various angles of irradiation from the light source 2 onto the surface of cap 1, by dividing the surface of the same cap 1 into a plurality of portions, and thereby upon repeating the inspection for a number of times, which requires more handling care and great time loss.

OBJECTS AND SUMMARY OF THE INVENTION

Therefore, it is an object of the present invention to propose a novel inspection apparatus for the surface of an object that is free from the defects inherent in the prior art apparatus.

According to an aspect of the present invention, there is provided an inspection apparatus comprising:

(a) a light source for irradiating an uneven surface of an object to be inspected;

(b) a photoelectric conversion sensor for picking up the uneven surface of the object and generating a video signal thereof;

(c) an electronic processor for processing the video signal to inspect the surface of the object;

(d) an optical mask located in front of the light source and for restricting the passage of the light from the light source with a predetermined pattern;

(e) light splitting means for dividing the light passed through the optical mask into two directions; and (f) light reflecting means for respectively reflecting thereon the lights in the two directions and for the reflected lights thereon to irradiate on the uneven surface of the object such that irregular light reflection on the uneven surface becomes substantially uniform.

According to another aspect of the present invention, there is provided a surface inspection apparatuses comprising:

(a) two light sources for irradiating an uneven surface of an object to be inspected;

(b) a photoelectric conversion sensor for picking up the uneven surface of the object and generating a video signal thereof;

(c) an electronic processor for processing the video signal to inspect the surface of the object; and (d) an optical mask located in front of each of the two light sources and for restricting the passage of the light from the light source with a predetermined pattern, whereby irregular light refection on the uneven surface becomes substantially uniform.

The above and other objects, features and advantages of the present invention will become apparent from the following detailed description in conjunction with the accompanying drawings through which like references designate the same elements and parts.

DESCRIPTION OF THE PREFERRED EMBODIMENTS

Figure 2:
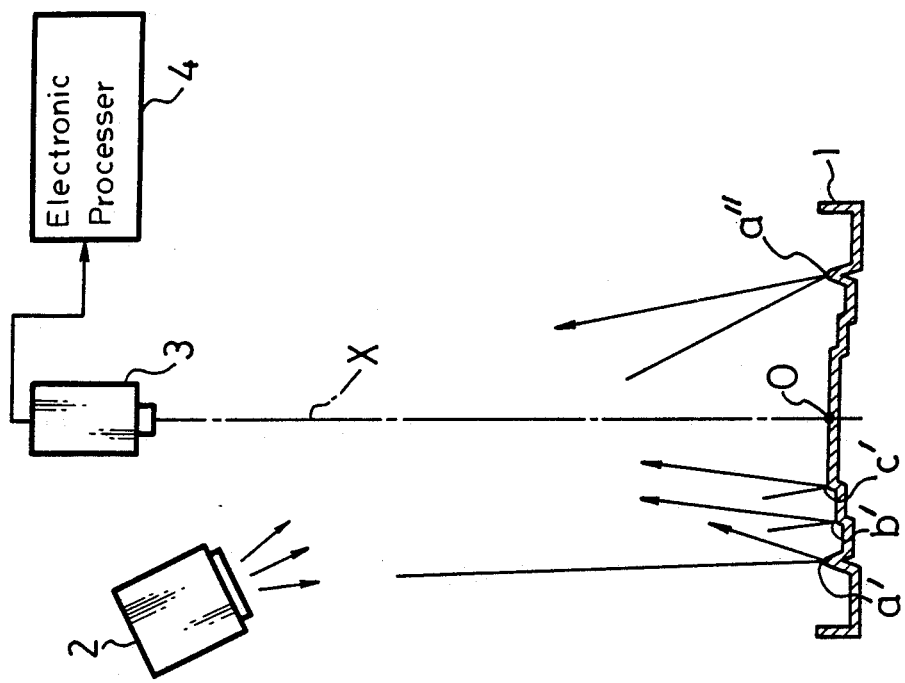
FIG. 2 is a schematic diagram showing a surface inspection apparatus under the prior art.
Figure 1A:
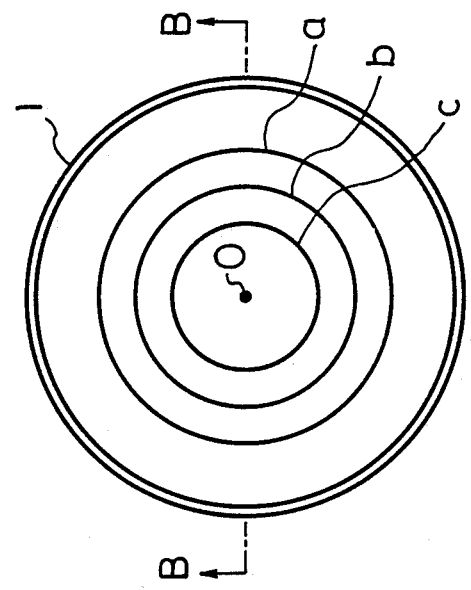
FIGS. 1A and 1B are respectively a top plan view of an object to be inspected and a cross-sectional view thereof.
Figure 1B:
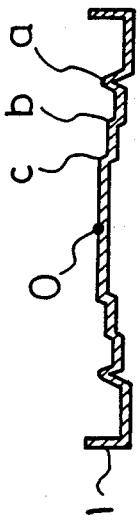
Figure 4:
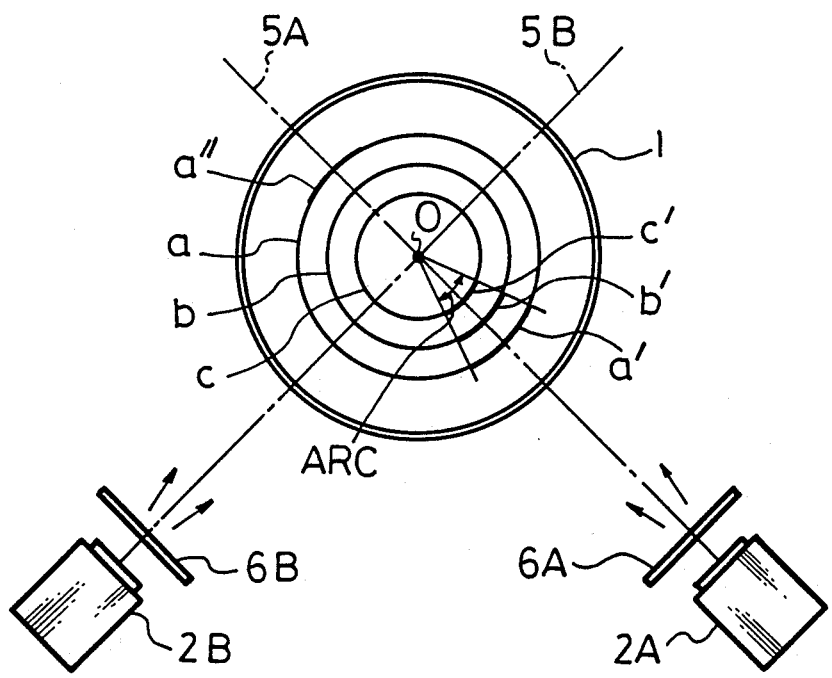
FIG. 4 is a schematic diagram illustrating the main portion of an embodiment of the present invention.

An embodiment of the present invention will be explained hereunder in reference with FIG. 4 and FIG. 5. It is noted that, in the embodiment of the present invention as shown in FIG. 4, the photoelectric conversion sensor (video camera) 3 and the electronic processor 4 are exactly the same as used in the prior art example as shown on FIG. 2, whereas the position of the video camera 3 against the object to be inspected that is a cap 1, is generally the same to the example as shown in FIG. 2, so that in order to simplize matters, they are not shown in FIG. 4. In other words, FIG. 4 shows only the main portion of the present invention.

In FIGS. 4, 2A and 2B designate light sources that respectively irradiate light on the surface of the cap 1 from an upper angled direction thereof. In this example, the light sources 2A and BB are positioned at an upper angled direction such that respective optical axes 5A and 5B thereof cross each other at the center 0 of the cap 1. Further, 6A and 6B denote optical masks that are placed in front of the light irradiating surface of the respective light sources 2A and 2B.

Figure 3:
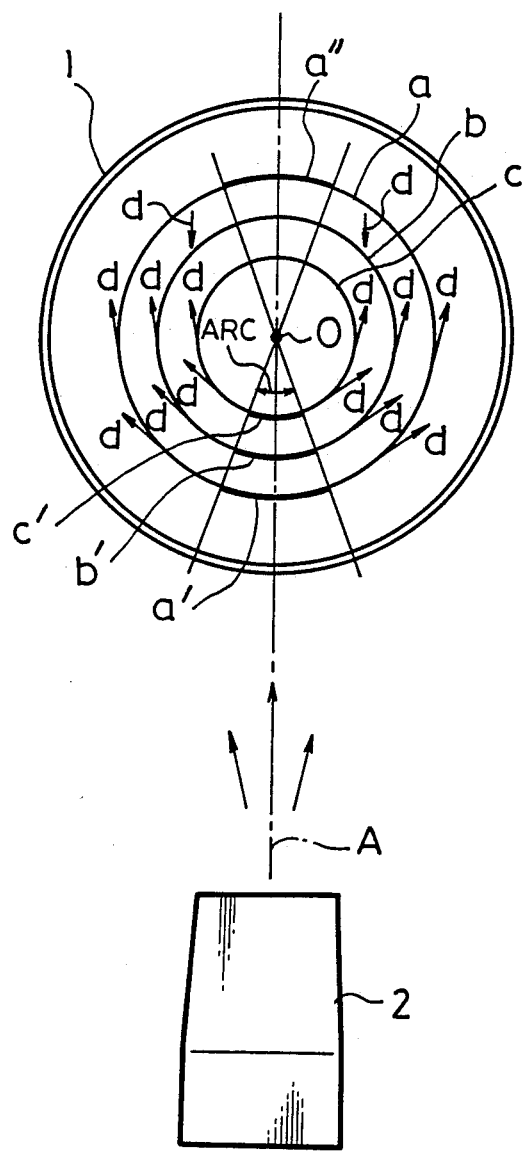
FIG. 3 is a schematic diagram that is used to explain the operation thereof.

Now, in the case that optical mask 6A is not used, the light from light source 2A is irregularly reflected on the portions a' or a'' of the ring-shaped protrusion portion a as well as on the portions b' and c' of edges b and c on the surface of the cap 1 of which an angular range ARC is smaller than 90° as compared to the other portions of the surface of the cap 1, as explained in connection with FIG. 2 and FIG. 3. The irregularly reflected lights are picked up directly by the video camera 3, so that the inspection becomes impossible as aforementioned. Therefore, in the example of the present invention, as shown in FIG. 4, an optical mask 6A is provided in front of the light irradiating surface of the light source 2A such that the light from the light source 2A does not reach at least the portions a', a'', b' and c'. Needless to say, the light from the light source 2A are incident on the surface of the cap 1 at other portions than the portions a', a'', b' and c'.

Figure 5:
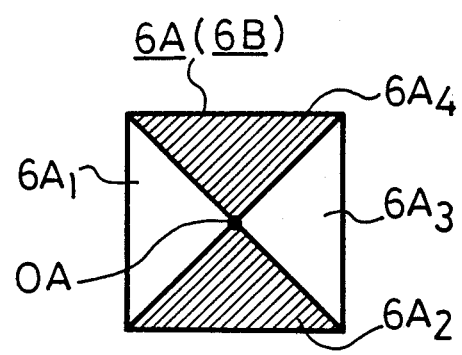
FIG. 5 and FIG. 6 are respectively the front views of embodiment of optical masks as shown on FIG. 4.

As the next step, an example of the optical mask 6A (or 6B) of the present invention will be explained in reference to its front view as shown in FIG. 5.

The optical mask 6A as shown in FIG. 5 is formed in such a manner that, for example, a transparent approximately square-shaped glass plate or the like is divided by two diagonal lines into four-triangled portions 6A1, 6A2, 6A3 and 6A4 and that two opposing-triangled portions such as in this example 6A2 and 6A4 are made opaque by applying, for example, black coating or the like (refer to hatched portions in FIG. 5) to the transparent glass plate.

Such above described optical mask 6A is placed in parallel to and in front of the light irradiation surface of the light source 2A such that the opaque portions 6A2 and 6A4 thereof are lined up in the vertical direction as shown in FIG. 4. In this case, the center OA of the optical mask 6A is placed to generally coincide with the optical axis 5A of the light source 2A. Therefore, the light from the light source 2A is partially shielded by the optical mask 6A so that it does no reach at least the hand drum-shaped portion including portions a', a'', b' and c' of the surface of the cap 1 and being generally symmetrically with respect the optical axis 5A, but reaches the other portions than those mentioned above of the surface of the cap 1. The light is then reflected on the other portions irregularly as used and the parts of the irregularly reflected lights enter the video camera 3 that is placed above the cap 1. The video signal from the video camera 3 is processed by the electronic processor 4 so that the inspection on the surface of cap 1 may be conducted. This inspection is, as aforementioned, the same as such apparatuses under the prior art. As above mentioned, by the use of optical mask 6A, the light from the light source 2A does not reach the hand drum-shaped surface portion of the cap 1 including its portions a', a'', b' and c' so that the inspection of these areas cannot be conducted. Therefore, according to the present invention, as shown in FIG. 4, other than the combination of the light source 2A and the optical mask 6A, a similar combination of the light source 2B and the optical mask 6B is placed with a predetermined angular distance, namely at least more than ½ of the angular range ARC of the arc like portions a', a"—and less than (180°−½ARC) apart from the former combination so as to irradiate the surface of cap 1 similar to the former combination. Accordingly, the combination of light source 2B and the optical mask 6B irradiate the hand drum-shaped area including portions a', a", b' and c' of the surface of cap 1 to which the light from the combination of light source 2A and optical mask 6A was shielded. Further, owing to the existence of the optical mask 6B, the light from light source 2B does not reach the areas on the surface of the cap 1 corresponding to the portions a', a", b' and c' for the light source 2A (these areas were already irradiated upon by the combination of light source 2A and optical mask 6A) but the light from the light source 2B reach the other portions superimposed on the light from light source 2A.

Figure 6:
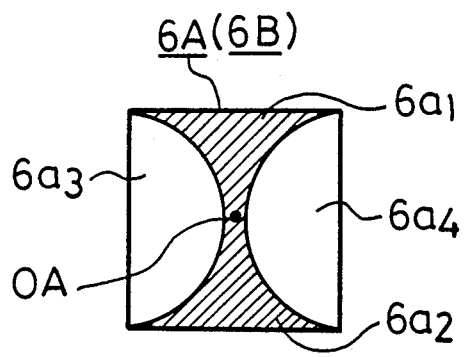

As above, according to the present invention, the portions such as the protruded portions a', a", b' and c' on the surface of the cap 1, which irregularly reflect the light from a single light source remarkably much as compared with the other portion and make the inspection impossible, are not irradiated by the light from the single light source by means of the optical mask, but are irradiated by the other light source that also has the optical mask. Therefore, the surface of cap 1 having on its surface such ring like or arc like unevenness can be positively and easily inspected at one inspection time. Further, for the optical masks 6A and 6B, it is not necessary to confine them with the patterns as shown on FIG. 5, and in essence, it can be any shape so long as the irradiation of light to the surface portions of the inspected object that cause unnecessary extreme irregular light reflections is shielded, such as shown in FIG. 6, for example, it may have shielding opaque portions 6a1 and 6a2 (the other portions 6a3 and 6a4 are transparent) of a hand drum-shaped portion which is symmetric with respect to the center OA and shown by the hatch.

Figure 7:
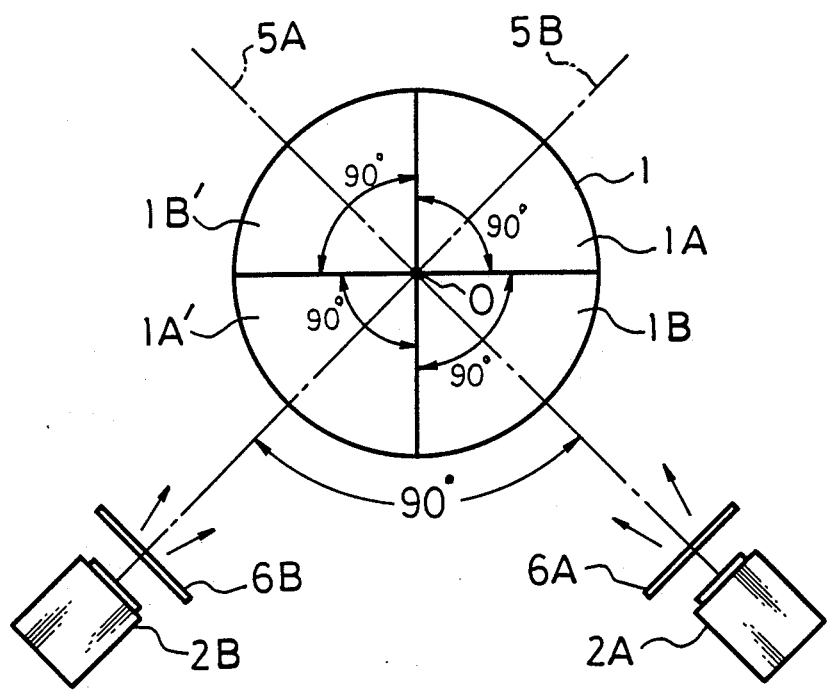
FIGS. 7, 8a, 8b, 9a, and 9a are schematic diagrams that show the main contents of other embodiments of the present invention respectively.

FIG. 7 is a top plan view of the main portion of another embodiment of the present invention in the same manner to FIG. 4. In this example, light sources that emit substantially parallel lights are used as light sources 2A and 2B, which are placed so that the optical axes 5A and 5B thereof cross each other at a substantially right angle at the center 0 of the cap 1. Further, the optical masks 6A and 6B which, for instance, contain patterns as shown in FIG. 5 are placed in the same manner as shown in the example of FIG. 4.

According to the example as shown in FIG. 7, by the combination of light source 2A and optical mask 6A, among the circle surface of cap 1, while fan-shaped portions 1A and 1A' of approximately 90° angular range, which are symmetrically located with respect to its center O and the optical axis 5A of the light source 2A, are irradiated upon, the other portions of the surface of cap 1 which are fan-shaped portions 1B and 1B' of approximately 90° angular range, that are symmetricity located in relation to the center O and the optical axis 5B of the other light source 2B, are shielded from the irradiation of the same light. In such case, since the wall like standing up portions or the arc-shaped portions a', b', c' and a", that are on the surface of cap 1 and which cause the extreme irregular light reflections, exist respectively within the non-irradiated fan like portions 1B and 1B' from the light source 2A, the impossibility of the inspection for the surface of cap 1 does not occur. Similarly, by the combination of the light source 2B and optical mask 6B, while the fan like portions 1B and 1B' that were not irradiated by the combination of light source 2A and optical mask 6A, are irradiated upon, the remainder fan like portions 1A and 1A' are not irradiated upon. Needless to say, the portions a', b', c' and a", that cause extreme irregular light reflections for the combination of light source 2B and optical mask 6B, are included in the non-irradiated portions 1A' and 1A by this combination so that they do not cause an impossibility of inspection for the surface of the cap 1.

As stated above, according to the example of the present invention, as shown in FIG. 7, the entire surface of cap 1 is uniformly irradiated by the combination of light source 2A and optical mask 6A as well as the combination of light source 2B and optical mask 6B without overlapping of lights, so that the normal irregular reflection of the light on the surface of the cap 1 is uniform and hence the inspection for the surface of cap 1 can be carried out more accurately.

Now then, while the examples of the present invention shown in FIG. 4 and FIG. 7 utilize the two light sources 2A and 2B, the present invention may be placed into practice by the use of a single light source with the proper arrangements for light-splitting means and light reflection means rather than using two light sources.

One example of such arrangement is explained in reference with FIG. 8 hereunder.

Figure 8A:
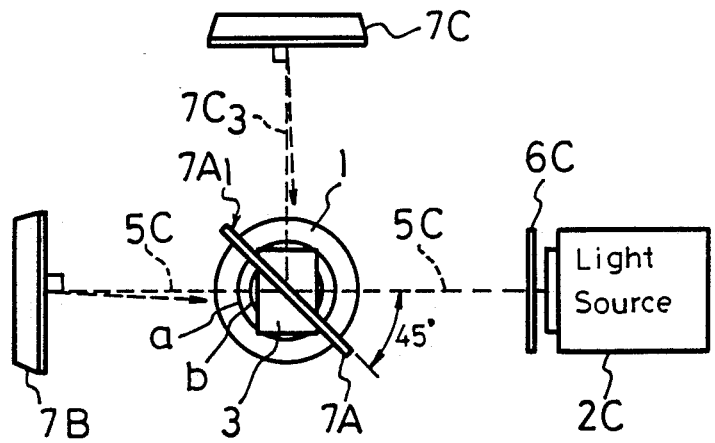
Figure 8B:
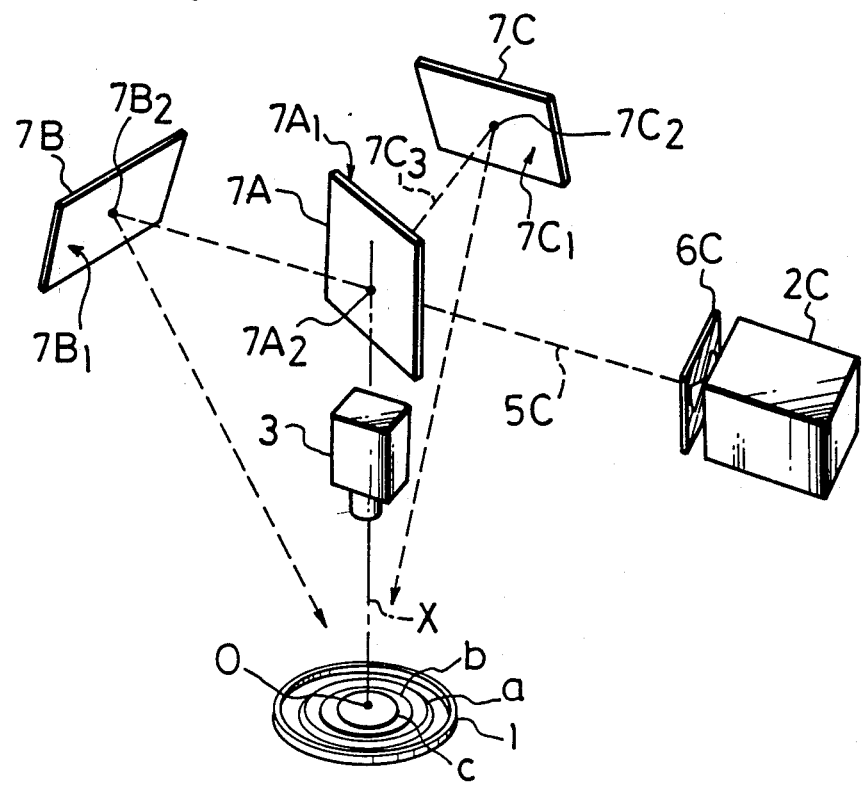

FIG. 8A is a top plan view of the main portions of such example, while FIG. 8B is a perspective view thereof. In this example, an optical mask 6C which is the same to the optical mask 6A or 6B, as an example, is placed in front of one light source 2C, light splitting means such as a half mirror 7A and two light reflection means such as mirrors 7B and 7C are used in order to irradiate the top surface of cap 1 as similar to, for example, the example as shown in FIG. 7. Further, the light source 2C emits substantially parallel light.

This example of the present invention will be hereunder explained in detail. The light source 2C is placed above the cap 1 in a manner that its optical axis 5C is generally in parallel to the top surface of cap 1 and at the same time crosses in right angle with the center axis X of cap 1. The half mirror 7A is placed such that its mirror surface 7A1 is about vertical and exists on the center axis X of cap 1, while its center 7A2 crosses with the optical axis 5C of the light source 2C as well as the center axis X of cap 1 and that its mirror surface 7A1 crosses the optical axis 5C with an angle of about 45°. Mirror 7B is placed to cross the optical axis 5C of light source 2C at right angle and tilted downwards such that its center 7B2 crosses the optical axis 5C of the light source 2C at the opposite side with respect to the light source 2C and its mirror surface 7B1 reflects the entire light from light source 2C as it passes through half mirror 7A and introduces the reflected light to the top surface of cap 1 as in the manner by which the light from light source 2A similarly reaches the cap 1 as in the example shown in FIG. 7.

At the same time, the other half mirror 7C is placed in a manner so that its center 7C2 crosses at right angle with the extension of a line 7C3 which is perpendicular to the optical axis 5C of light source 2C at the center 7A2 of the half mirror 7A, whereas its mirror surface 7C1 is tilted to the line 7C3 downwards to reflect again the light from light source 2C that is reflected on half mirror 7A and to introduce the second reflected light to the top surface of cap 1 such as the light from the light source 2B in the example as shown on FIG. 7.

Accordingly, in the example shown in FIG. 8, although the light source is only one, by the functions of the half mirror 7A, the mirrors 7B and 7C will function in the same manner to the two light sources 2A and 2B in the example as shown in FIG. 7. Therefore, the function and effects are about the same as those of the example as shown in FIG. 7.

In addition, in the example shown in FIG. 8, as therein indicated, the photoelectric conversion sensor 3 is placed under the half mirror 7A.

Figure 9A:
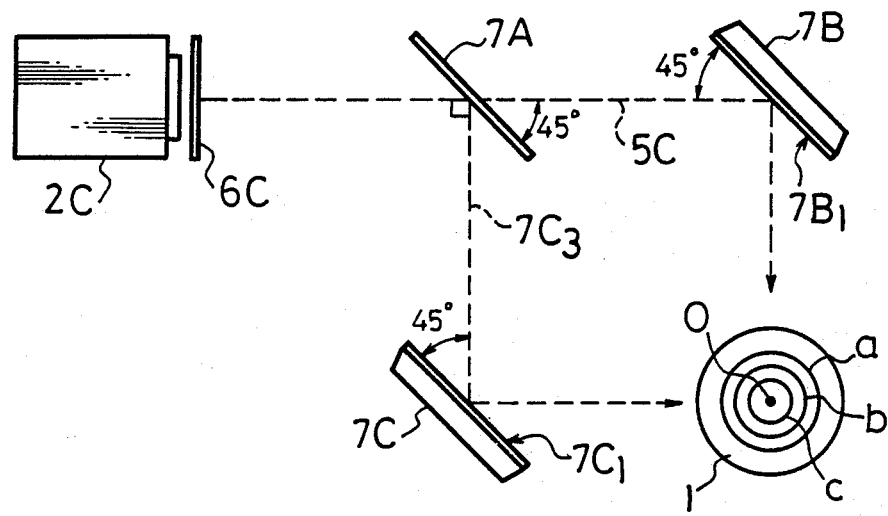
Figure 9B:
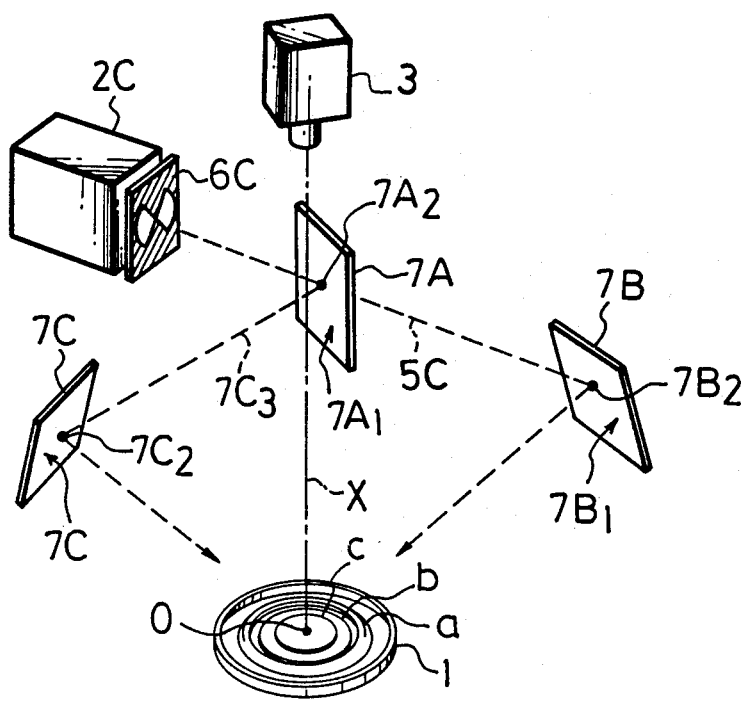

FIGS. 9A and 9B illustrate a top plan view and a perspective view of the main portion of a further embodiment of the present invention. The structural elements of the example in FIG. 9 are generally the same to the structural elements as shown in FIG. 8. Therefore, the references in FIG. 9 refer to the same elements as in FIG. 8.

The main difference between the embodiments as shown in FIG. 9 and FIG. 8 exists in the difference of the tilted angle of the mirrors 7B and 7C, and in that the light axis 5C of the light source 2C is offset against the optical axis of the photoelectric conversion sensor 3 or the center axis X of the cap 1.

In other words, as shown in FIG. 9A, the mirror surface 7B1 of the mirror 7B is tilted by about 45° against the optical axis 5C of the light source 2C while the mirror surface 7C1 of the mirror 7C is also tilted by about 45° against the extension of line 7C3. Therefore, except for the fact that the mirror surfaces 7B1 and 7C1 of the mirrors 7B and 7C are respectively tilted downwards, they are in parallel relations to each other. Further, it is needless to say that both of the mirror surfaces 7B1 and 7C1 are tilted downwards against the optical axis 5C and line 7C3 in the manner as shown on FIG. 9B such that the reflected lights thereon irradiate the cap 1 that is located thereunder. In this case also, the light that is emitted from the light source 2C is split into two directions by the half mirror 7A which are respectively reflected on both mirror surfaces 7B1 and 7C1 and the reflected lights irradiate the surface of cap 1 to cross each other at substantially right angle at the center 0 of the cap 1 in a similar manner to the example as shown on FIGS. 7 and 8. Further, the photoelectric conversion sensor 3 is placed so that its optical axis coincides with the center axis X of cap 1 about the half mirror 7A. Accordingly, the functions and effects thereof shown in FIG. 9 are substantially the same as those of the examples in FIG. 7 and FIG. 8.

It is noted that in the examples shown in FIG. 8 and FIG. 9, though not shown, the half mirror 7A, mirrors 7B and 7C are supported by an adequate adjustable holder respectively and that the angles thereof can be adjusted.

Further, as for the optical mask, instead of placing the same in the front of the light source, it may be placed either in front of the mirror surface of the mirror 7A or in front of each of the mirrors 7B and 7C, respectively. Needless to say, equally in the examples shown in FIG. 8 and FIG. 9, the output from the photoelectric conversion sensor 3 is processed by the electronic processor 4 so that the inspection of flaws on the surface of the inspected object may be conducted.

As above stated, according to the present invention, the uneven surface of the inspected object is irradiated by the use of particular optical masks applied to the light source such that the irregular light reflection on the uneven surface becomes uniform so that such type of inspected objects may be inspected for the entire surface by a one time inspection positively and easily.

According to the examples as shown in FIG. 8 and FIG. 9, in addition to the effects of the examples shown in FIG. 4 as well as FIG. 7, a single combination of the expensive light source and optical mask is sufficient.

It will be apparent that many modifications and variations could be effected by one skilled in the art without departing from the spirits or the scope of the novel concepts of the present invention so that the spirits or the scope of the novel concepts of the invention should be determined by the appended claims only.

I claim as my invention:

1. A surface inspection apparatus comprising:
   (a) a light source for irradiating an uneven surface of an object to be inspected;
   (b) a photoelectric conversion sensor for picking up the uneven surface of the object and generating a video signal thereof;
   (c) an electronic processor for processing the video signal to inspect the surface of the object;
   (d) an optical mask formed of two opaque portions and two transparent portions which are arranged alternately around the center of the optical mask, the two opaque portions being symmetrical to each other with respect to the center of the optical mask, the two transparent portions being also symmetrical to each other with respect to the center of the optical mask, said optical mask being located in front of the light source with the center of the former being coincident with the optical axis of the light source;
   (e) light splitting means for dividing the light passed through the optical mask into two directions intersecting at substantially 90 degrees; and
   (f) two light reflecting means for respectively reflecting thereon the lights from the light splitting means in such a manner that reflected lights intersect each other at substantially 90 degrees at the center of the surface of the object so that irregular light reflection on the uneven surface becomes substantially uneven.

2. A surface inspection apparatus as claimed in claim 1, wherein said light source emits substantially parallel light.

3. A surface inspection apparatus as claimed in claim 1, wherein said light splitting means is half mirror.

4. A surface inspection apparatus as claimed in claim 1, wherein said optical mask is formed of a substantially square-shaped transparent plate on which an opaque portion with a predetermined patter is formed.

5. A surface inspection apparatus as claimed in claim 4, wherein said opaque portion is formed in such a manner that the surface of said transparent plate is divided by two diagonal lines into four-triangled portions and a pair of opposing triangled portions are made opaque.

6. A surface inspection apparatus comprising:
   (a) two light sources each for obliquely irradiating an uneven surface of an object to be inspected from its upper side, said two light sources are located such that their optical axes cross each other at a substantially right angle at the center of the surface of said object;
   (b) a photoelectric conversion sensor for picking up the uneven surface of the object and generating a video signal thereof;

(c) an electronic processor for processing the video signal to inspect the surface of the object; and (d) an optical mask located in front of each of the two light sources and for restricting the passage of the light from each of the light sources in such a manner that the light passed through the optical mask located in front of one of the light sources irradiate the surface of the object except for two surface portions thereof which are substantially the same in shape, symmetrical with respect to the optical axis of the other light and an angle of each of the two surface portions at the center of the surface of the object is substantially 90 degrees with the optical axis of the one light source as the center, whereby the irregular light reflection on the uneven surface becomes substantially uniform.

7. A surface inspection apparatus as claimed in claim 6, wherein each of said light sources emits substantially parallel light.

8. A surface inspection apparatus as claimed in claim 6, wherein said optical mask is formed of a substantially square-shaped transparent plate on which an opaque portion with a predetermined patter is formed.

9. A surface inspection apparatus as claimed in claim 8, wherein said opaque portion is formed in such a manner that the surface of said transparent plate is divided by two diagonal lines into four-triangled portions and a pair of opposing triangled portions are made opaque.

* * * * *

UNITED STATES PATENT AND TRADEMARK OFFICE
CERTIFICATE OF CORRECTION

PATENT NO. : 4,868,404

DATED : September 19, 1989

INVENTOR(S) : HAJIME YOSHIDA

It is certified that error appears in the above-identified patent and that said Letters Patent is hereby corrected as shown below:

On the title page, under item [19], "Hajime" should be --Yoshida-- and in item [75], "Yoshida Hajime" should be --Hajime Yoshida--.

Column 8, line 44 "uneven" should be --uniform--

Column 8, line 53 "patter" should be --pattern--

Column 10, line 9 "patter" should be --pattern--

Signed and Sealed this

Seventh Day of August, 1990

Attest:

HARRY F. MANBECK, JR.

*Attesting Officer*      *Commissioner of Patents and Trademarks*